United States Patent [19]

Saeki et al.

[11] Patent Number: 4,996,372

[45] Date of Patent: Feb. 26, 1991

[54] PROCESS FOR OXIDIZING 2,6-DIISOPROPYLNAPHTHALENE

[75] Inventors: Kenji Saeki, Ohtake; Hiroshi Fukuhara, Ichihara; Tokinori Agoo, Hiroshima; Toru Taguchi; Hisaya Miki, both of Iwakuni; Yutaka Haneda; Sadao Yoshimoto, both of Iwakuni, all of Japan

[73] Assignee: Mitsui Petrochemical Industries, Ltd., Tokyo, Japan

[21] Appl. No.: 473,105

[22] Filed: Feb. 2, 1990

Related U.S. Application Data

[63] Continuation of Ser. No. 10,136, filed as PCT JP86/00215 on Apr. 28, 1986, abandoned.

[30] Foreign Application Priority Data

Sep. 20, 1985 [JP] Japan .................. 60-209275
Sep. 20, 1985 [JP] Japan .................. 60-209276

[51] Int. Cl.$^5$ ............................ C07C 39/14
[52] U.S. Cl. ........................ 568/717; 560/139; 568/565; 568/569
[58] Field of Search ............ 568/741, 565, 568, 569, 568/717

[56] References Cited

U.S. PATENT DOCUMENTS

| | | | |
|---|---|---|---|
| 2,776,322 | 1/1957 | Webster | 568/741 |
| 3,360,570 | 12/1967 | Bewley | 568/565 |
| 3,662,000 | 5/1972 | Ito et al. | 260/593 |
| 3,839,461 | 10/1974 | Aoshima | 568/565 |
| 3,933,921 | 1/1976 | Suda | 568/569 |
| 4,463,198 | 7/1984 | Nowak | 568/741 |
| 4,469,899 | 9/1984 | Nakamura | 568/768 |
| 4,503,262 | 3/1985 | Gupton | 568/569 |

FOREIGN PATENT DOCUMENTS

| | | | |
|---|---|---|---|
| 55-79334 | 6/1980 | Japan | 568/768 |
| 61-93156 | 5/1986 | Japan . | |
| 61-100558 | 5/1986 | Japan | 568/565 |
| 61-191638 | 8/1986 | Japan | 568/569 |
| 910735 | 11/1962 | United Kingdom | 568/768 |

OTHER PUBLICATIONS

Wagner, "Synthetic Organic Chemistry," pp. 479-483 (1953).

*Primary Examiner*—Michael L. Shippen
*Attorney, Agent, or Firm*—Sherman and Shalloway

[57] ABSTRACT

In a process for producing 2,6-dihydroxynaphthalene from 2,6-diisopropylnaphthalene, 2,6-diisopropylnaphthalene is oxidized in the presence of a specific proportion of a basic compound to hydroxylate or hydroperoxylate 2,6-diisopropylnaphthalene in a high conversion, and the resulting intermediate is then subjected to acid cleavage in the presence of hydrogen peroxide to produce 2,6-dihydroxynaphthalene in a high yield. The yield of 2,6-dihydroxynaphthalene increases by subjecting the reaction mixture containing the above intermediate to a purifying operation or dehydrating operation or adding acetone to it before it is submitted to the acid cleavage. 2,6-Dihydroxynaphthalene may be reacted with acetic anhydride to obtain 2,6-diacetoxynaphthalene.

12 Claims, No Drawings

PROCESS FOR OXIDIZING 2,6-DIISOPROPYLNAPHTHALENE

This application is a continuation of application Ser. No. 07/010,136 filed as PCT JP86/00215 on Apr. 28, 1986, now abandoned.

TECHNOLOGICAL FIELD

This invention relates to a process for oxidizing 2,6-diisopropylnaphthalene, and processers for producing 2,6-dihydroxynaphthalene and 2,6-diacetoxynaphthalene. More specifically, this invention relates to a process for oxidizing the isopropyl groups of 2,6-diisopropylnaphthalene to hydroxypropyl or perhydroxypropyl groups, and to a process for producing 2,6-dihydroxynaphthalene and 2,6-diacetoxynaphthalene from the oxidation product of the above process.

BACKGROUND TECHNOLOGY 2,6-Dihydroxynaphthalene (to be referred to sometimes as 2,6-DHN hereinafter) can be obtained by oxidizing 2,6-diisopropylnaphthalene (to be referred to sometimes as 2,6-DIPN hereinafter) to form 2,6-diisopropylnaphthalene dihydroperoxide (to be referred to sometimes as DHP hereinafter) and acid-cleaving the product in the presence of an oxidation catalyst. 2,6-Diisopropylnaphthalene is useful as a raw material for synthetic resins, synthetic fibers, medicines, agricultural chemicals, dyes, etc.

A batchwise process for oxidizing p-diisopropylbenzene, different from 2,6-diisopropylnaphthalene, has previously been known which comprises oxidizing p-diisopropylbenzene with molecular oxygen at a temperature of 80° to 120° C. until the concentration of hydroperoxide calculated as p-diisopropylbenzene monohydroperoxide in the oxidation reaction product becomes at least 115% by weight while optionally feeding an aqueous alkaline solution having a pH higher than 10 so as to maintain the pH of the oil layer in the reaction system at 9 to 11 during the reaction and while on the other hand, optionally removing the aqueous layer from the reaction system so as to maintain the amount of water in the reaction system at 5 to 60% by weight (see Japanese Patent Publication No. 44066/1980 and Japanese Laid-Open Patent Publication No. 72144/1973).

In the aforesaid oxidation of p-diisopropylbenzene, the amount of water in the aqueous layer of the reaction system is adjusted to 5 to 60% by weight while the pH of the oil layer is maintained at 9 to 11 during the reaction.

Japanese Laid-Open Patent Publication No. 34,138/1976 discloses a process which comprises bringing beta-isopropylnaphthalene into intimate contact with molecular oxygen in an aqueous alkaline medium with stirring at about 75° to 100° C. in the presence of 25 to 1,000 ppm, based on beta-isopropylnaphthalene, of a specific nickel (II), rhodium (I) or Ir compound (catalyst); separating the reaction mixture into an aqueous layer and an oily layer; and recovering beta-isopropylnaphthalene hydroperoxide from the oily layer.

Likewise, British Patent Specification No. 654,035 discloses a process for producing beta-isopropylnaphthalene hydroxide, which comprises reacting beta-isopropylnaphthalene with molecular oxygen in the liquid phase at an elevated temperature in the substantial absence of a heavy metal oxidation catalyst.

The processes described in the above-cited Japanese Laid-Open Patent Publication No. 34,138/1976 and British Pat. No. 654,035 are for the oxidation of monoisopropylnaphthalene and not for the oxidation of diisopropylnaphthalene.

U.S. Pat. No. 4,503,262 discloses a process for converting 2,6-diisopropylnaphthalene to 2,6-diisopropylnaphthalene hydroperoxide, which comprises dissolving the 2,6-diisopropylnaphthalene in a $C_{5-14}$ aliphatic hydrocarbon and bringing the solution into contact with an oxygen-containing gas in a basic medium at an elevated temperature in the range of about 50° C. to about 100° C. under atmospheric pressure in the presence of a catalyst selected from the group consisting of oxides, hydroxides and organic acid salts of heavy metals, and mixtures thereof.

U.S. Pat. No. 4,503,262 discloses that the process described there has the advantage of increasing the rate of the reaction and improving the yield and purity of hydroperoxide.

It is an object of this invention to provide a process for oxidizing 2,6-diisopropylnaphthalene with molecular oxygen.

Another object of this invention is to provide a process which comprises oxidizing 2,6-diisopropylnaphthalene with molecular oxygen to form an oxidation product composed mainly of 2,6-diisopropylnaphthalene dihydroperoxide, monohydroxymonoperoxide and dihydroxide in a high conversion from 2,6-diisopropylnaphthalene.

Still another object of this invention is to provide a process for producing 2,6-dihydroxynaphthalene in a high yield which comprises subjecting the oxidation product obtained by the above oxidation process of the invention to oxidation and acid cleavage using hydrogen peroxide.

Yet another object of this invention is to provide a process in which purified 2,6-dihydroxynaphthalene is recovered in a high yield from the reaction mixture containing 2,6-dihydroxynaphthalene obtained by the above oxidation and acid cleavage.

A further object of this invention is to provide a process for producing 2,6-diacetoxynaphthalene, which comprises converting 2,6-dihydroxynaphthalene obtained by the above oxidation and acid cleavage into 2,6-diacetoxynaphthalene and recovering it.

Additional objects and advantages of this invention will become apparent from the following description.

DISCLOSURE OF THE INVENTION

According to this invention, the above objects and advantages of this invention are firstly achieved by a process for oxidizing 2,6-diisopropylnaphthalene, which comprises oxidizing 2,6-diisopropylnaphthalene with molecular oxygen in the presence of a base, said oxidation reaction being performed by using at least 0.06 gram-equivalent, per mole of 2,6-diisopropylnaphthalene as the starting material, of a basic compound until the reaction is stopped.

This oxidation process of the invention gives a product resulting from oxidation of at least one of the isopropyl groups of 2,6-diisopropylnaphthalene to a 2-hydroxyprop-2-yl or 2-perhydroxyprop-2-yl group as a main oxidation product. It is not the purpose of this invention to perform the above oxidation until the main oxidation product is a product resulting from oxidation of the isopropyl groups of 2,6-diisopropylnaphthalene to a higher oxidation state to form formyl or carboxyl groups.

Specifically, the main oxidation product formed by the oxidation process of this invention consists of oxidation products selected from the dihydroperoxide, monohydroxymonohydroperoxide, dihydroxide, monohydroxide and monoperoxide of 2,6-diisopropyl-naphthalene. In particular, the dihydroxyperoxide, monohydroxymonohydroperoxide and dihydroxide occupy a greater portion of the oxidation product, for example at least 50 mole % based on the oxidized 2,6-diisopropylnaphthalene.

In oxidizing 2,6-diisopropylnaphthalene with molecular oxygen in the presence of a base in the oxidation process of this invention, the oxidation reaction is carried out by using at least 0.06 gram-equivalent, per mole of 2,6-diisopropylnaphthalene used as the starting material, of a basic compound (namely, by adding at least 0.06 gram-equivalent, per mole of 2,6-diisopropylnaphthalene as the starting material, of a basic compound to the reaction system) until the reaction is stopped.

This amount is understood as the amount of the basic compound used (charged) based on the amount charged of 2,6-diisopropylnaphthalene on an average per unit time. The basic compound is used preferably in an amount of 0.1 to 3.0 gram-equivalents, more preferably 0.2 to 1.0 gram-equivalent, on the same basis as above. The basic compound to be present in the reaction system may be added at a time to the reaction system before the start of the reaction, or may be added in some portions to the reaction system. Preferably, one portion of the basic compound is added to the reaction system before the start of the reaction, and the remaining portions, to the reaction system during the reaction.

Examples of suitable basic compounds include alkali metal compounds such as sodium hydroxide, potassium hydroxide, sodium hydrogen carbonate, potassium hydrogen carbonate, sodium carbonate and potassium carbonate, and alkaline earth metal compounds such as calcium hydroxide, magnesium hydroxide and strontium hydroxide. These basic compounds may be used singly or in combination. The alkali metal compounds are preferred, and potassium hydroxide and sodium hydroxide are especially preferred.

The oxidation reaction in this invention is carried out in the presence of the basic compound, preferably in the further presence of an aqueous medium. Owing to the presence of the basic compound, the pH of the aqueous phase in the oxidation reaction system is preferably 9 to 14, more preferably 11 to 14, especially preferably 12 to 14. When the basic compound is added as an aqueous solution to the reaction system, it may preferably be added as an aqueous solution having a concentration of 1 to 25% by weight.

According to the oxidation process of this invention using the aforesaid specific proportion of the basic compound, 2,6-diisopropylnaphthalene is oxidized in a high conversion, for example, in a conversion of at least 80%, preferably at least 95%, more preferably at least 99%. In this invention, the reaction product composed mainly of the dihydroperoxide, monohydroxymonohydroperoxide and dihydroxide can be obtained as an oxidation product. Furthermore, according to the oxidation process of this invention, the rate of the reaction is high so that even when the reaction temperature is lowered, a permissible reaction rate can be achieved.

The oxidation process of this invention is usually carried out by mixing an aqueous phase containing the basic compound and an organic phase containing 2,6-diisopropylnaphthalene with mechanical stirring to create an emulsified condition, and blowing molecular oxygen into this condition. The emulsified condition may be formed by mechanically mixing the aqueous phase and the organic phase with stirring. The co-presence of a known emulsifier such as sodium stearate at this time facilitates emulsification. Intense stirring is preferred.

The organic phase may be composed of 2,6-diisopropylnaphthalene itself. Alternatively, when the reaction is performed in the presence of an organic solvent in the reaction system, it may be composed of 2,6-diisopropylnaphthalene and the organic solvent.

The organic solvent may, preferably, include aromatic hydrocarbons substituted by secondary alkyl, benzene, halogenated aromatic hydrocarbons, halogenated aliphatic hydrocarbons, aliphatic saturated hydrocarbons, alicyclic hydrocarbons, nitro compounds, nitriles, sulfoxides (and so on).

Preferably, the aromatic hydrocarbons substituted by secondary alkyl are, for example, those of the following formula (I)

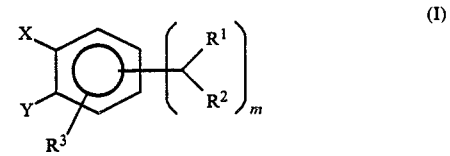

wherein $R^1$ and $R^2$ represent a lower alkyl group, $R^3$ represents hydrogen, a lower alkyl group, a lower alkyl-substituted phenyl group or halogen, X and Y are both hydrogen atoms, or may be bonded to each other to form a substituted or unsubstituted tetralin or naphthalene ring together with the benzene ring to which they are bonded, and m represents an integer of 1, 2 or 3, with the proviso that m

groups may be identical or different.

Specific examples of these compounds are alkylbenzenes such as cumene, diisopropylbenzene, triisopropylbenzene, methylisopropylbenzene (cymene), fluoroisopropylbenzene, chloroisopropylbenzene, bromoisopropylbenzene, sec-butylbenzene, sec-amylbenzene and sec-hexylbenzene; biphenyls such as diisopropylbiphenyl; tetralins such as isopropyltetraline; and alkylnaphthalenes such as beta-isopropylnaphpthalene. Of these, isopropylbenzenes such as cumene, diisopropylbenzene, triisopropylbenzene and halogenated isopropylbenzene are preferably used.

Examples of the halogenated aromatic hydrocarbons are chlorobenzene, dichlorobenzene, bromobenzene, dibromobenzene, fluorobenzene and difluorobenzene.

Examples of the halogenated aliphatic hydrocarbons are chloroform, carbon tetrachloride, dichloroethane, trichloroethane and $H(CF_2)_nCl$ (where n is 5 to 10).

Examples of the aliphatic saturated hydrocarbons are hexane, heptane, octane, nonane, decane, undecane and dodecane.

Examples of the alicyclic hydrocarbons are cyclohexane, cycloheptane, chlorocyclohexane and dichlorocyclohexane.

Examples of the nitro compounds are nitrobenzene and nitromethane.

Examples of the nitriles are benzonitrile and acetonitrile.

Examples of the sulfoxides are dimethyl sulfoxide, dimethylsulfone and tetramethylenesulfone (sulfolane).

The use of halogenated aromatic hydrocarbons such as chlorobenzene and dichlorobenzene is preferred because such solvents are easily available and permit easy after-treatment operation after the reaction. The amount of the organic solvent is preferably 20 to 1000 parts by weight, more preferably 50 to 300 parts by weight, per 100 parts by weight of 2,6-diisopropylnaphthalene.

Usually, the basic aqueous phase in the reaction mixture preferably occupies 5 to 80% by weight, especially 20 to 70% by weight, of the reaction mixture.

The 2,6-diisopropylnaphthalene used as a reaction material is preferably of high purity, and 2,6-diisopropylnaphthalene having a purity of at least 85% can be used as a starting material in the oxidation process of this invention.

Molecular oxygen may be an oxygen gas alone, but a mixture of oxygen and an inert gas, for example air, usually suffices. The amount of molecular oxygen required is usually 5 to 15Nl/hour, calculated as oxygen gas, per 100 g of 2,6-diisopropylnaphthalene charged for the oxidation reaction, but is not particularly limited.

The oxidation reaction temperature is usually 70° to 150° C., preferably 80° to 110° C. The reaction time varies depending upon the reaction temperature and other conditions, but is usually 6 to 100 hours, preferably 7 to 50 hours. By the oxidation reaction under these conditions, a 2,6-diisopropylnaphthalene conversion of at least 80% can be obtained. The reaction is usually carried out under atmospheric pressure, but as required, may be carried out under atmospheric pressure to an elevated pressure of 50 kg/cm$^2$, or under reduced pressure.

The reaction mixture obtained by performing the oxidation process of this invention as above contains such oxidation products as the dihydroperoxide, monohydroxymonohydroperoxide and dihyroxide of 2,6-diisopropylnaphthalene. The composition of the oxidation reaction mixture can be determined, for example, by separating it into an organic phase and an aqueous phase, extracting the aqueous phase with ether, combining the extract with the organic phase, and subjecting the resulting mixture to liquid chromatography.

Investigations of the present inventors have shown that the dihydroperoxide, monohydroxymonohydroperoxide and dihydroxide contained in the reaction mixture obtained by performing the oxidation process of this invention as above can be converted in one step to 2,6-dihydroxynaphthalene by subjecting them to acid cleavage in the presence of hydrogen peroxide.

The acid cleavage may be carried out on the oxidation product obtained by oxidizing these compounds with hydrogen peroxide, but preferably, it is carried out in the presence of hydrogen proxide. In either case, hydrogen peroxide converts the monohydroxide or dihydroxide of 2,6-diisopropylnaphthalene contained in the oxidation reaction product to 2,6-diisopropylnaphthalene dihydroperoxide.

In order to subject the reaction mixture of oxidation to acid cleavage, the reaction mixture is then subjected to an after-treatment comprising optionally removing the reaction solvent, adding a water-insoluble or sparingly water-soluble organic solvent to form an organic phase and an aqueous phase, separating the organic phase, and subjecting the separated organic phase to acid cleavage.

The removal of the reaction solvent optionally carried out before adding the water-insoluble or sparingly water-soluble organic solvent is for the purpose of removing part or the whole of the organic solvent when the oxidation reaction mixture is obtained by performing the oxidation reaction in the presence of the organic solvent.

Ketones or hydrocarbons, for example, are used as the water-insoluble or sparingly water-soluble organic solvents. The ketones are especially preferred.

Water-insoluble dialkylketones having 5 to 11 carbon atoms are preferably used as the water-insoluble or sparingly water-soluble ketones. Examples of the ketones are methyl isopropyl ketone, methyl isobutyl ketone (MIBK), diisobutyl ketone, diisopropyl ketone, ethyl isobutyl ketone, propyl butyl ketone and amyl butyl ketone. Of these, methyl isobutyl ketone is especially preferred in this invention.

The reason for using the water-insoluble or sparingly water-soluble organic solvent is as follows: In particular, when the conversion of 2,6-diisopropylnaphthalene does not reach at least 80%, the proportion of an oxidation product which is liquid at the high temperature used in the oxidation reaction but solidifies when cooled to room temperature, for example 2,6-diisopropylnaphthalene dihydroperoxide, increases in the oxidation reaction mixture and there is created a condition in which the solidified oxidation product takes in it the aqueous phase containing the basic compound. The water-insoluble or sparingly water-soluble organic solvent is used to separate the aqueous phase efficiently from this condition and form an organic phase containing the oxidation product. The water-insoluble or sparingly water-soluble organic solvent is excellent in that it forms an organic phase which contains a small amount of the basic compound and from which water can be easily removed by distillation. If the organic phase contains a large amount of the basic compound or water, acid cleavage of the organic phase gives the desired 2,6-dihydroxynaphthalene in a markedly decreased yield.

Preferably, the water-insoluble or sparingly water-soluble organic solvent, especially a ketone, is added in an amount of 0.2 to 10 parts by weight, especially 0.3 to 5 parts by weight, per part by weight of the oxidation reaction mixture to which it is to be added. The organic solvent is brought into sufficient contact with the oxidation reaction mixture, and then the mixture is maintained at a temperature of usually 30° to 90° C. whereby an organic phase and an aqueous phase are formed. Then, the organic phase is separated from the aqueous phase and recovered. The aqueous phase containing the basic compound used at the time of the oxidation reaction is usually discarded. The organic phase is washed with water if required. According to this invention in which the water-insoluble or sparingly water-soluble organic solvent is used, an organic base having a very low basic compound content can be obtained as stated above. For example, in a preferred embodiment in which methyl isobutyl ketone is used, it is even possible to separate and recover an organic phase containing not more than 20 ppm of the basic compound.

According to the present invention, the organic phase containing the water-insoluble or sparingly water-soluble organic solvent is then subjected to acid cleavage. The organic phase separated in the previous step may directly be subjected to acid cleavage. Preferably, the separated organic phase is subjected to distillation to remove water as much as possible by azeotropic distillation, and then subjected to acid cleavage. By removing a maximum of water, the yield of 2,6-dihydroxynaphthalene as the final desired product of acid cleavage can be increased. Furthermore, when water is removed from the organic phase by azeotropic distillation, acetone is added to the organic phase, and the mixture is subjected to acid cleavage, the yield of 2,6-dihydroxynaphthalene is further increased although no entirely clear reason can be assigned to it. The azeotropic distillation can be advantageously carried out usually under a reduce pressure of 50 to 200 mHg and at a temperature of 50° to 90° C. Desirably, dehydration is carried out by azeotropic distillation to a water content of not more than 3% by weight, particularly not more than 1% by weight.

Usually, acetone is added in an amount of 5 to 1200 parts by weight per 100 parts by weight of the residue from the azeotropic distillation.

A source of hydrogen peroxide used in the acid cleavage may be hydrogen peroxide, an aqueous solution of hydrogen peroxide, or a substance which generates hydrogen peroxide under the reaction condition, for example sodium peroxide or calcium peroxide. The aqueous solution of hydrogen peroxide is preferred. Hydrogen peroxide is believed to perform the action of converting the hydroxyl groups of the monohydroxymonohydroperoxide and dihydroxide of 2,6-diisopropylnaphthalene into hydroperoxy groups and converting the monohydroxymonoperoxide and dihydroxide to dihydroperoxide. The dihydroperoxide undergos acid cleavage to form 2,6-dihydroxynaphthalene.

The source of hydrogen peroxide may be used in an amount of preferably 0.9 to 2 moles, more preferably 1.0 to 1.5 moles, per mole of the hydroxyl groups of carbinols such as the monohydroxymonoperoxide, dihydroxide and monohydroxide of 2,6-dihydroxynaphthalene. By using hydrogen peroxide in such a proportion, the formation of by-products based on the condensation of these carbinols can be markedly inhibited.

As an acid catalyst in the acid cleavage reaction, there are preferably used inorganic acids such as sulfuric acid, hydrochloric acid and phosphoric acid, strongly acidic ion exchange resins, solid acids such as silica gel and silica-alumina, organic acids such as chloroacetic acid, methanesulfonic acid, benzenesulfonic acid and toluenesulfonic acid, and heteropolyacids such as phosphotungstic acid and phosphomolybdic acid. The acid catalyst may be directly added to the reaction system. When it has solubility, it may be dissolved in a suitable inert solvent and then added to the reaction system. The amount of the acid catalyst, although varying depending upon its type and the reaction conditions, is usually 0.005 to 10% by weight, preferably 0.01 to 10%, based on the entire reaction mixture.

The acid cleavage reaction is carried out preferably at 0° to 100° C., more preferably 20° to 80° C.

After the reaction, 2,6-dihydroxynaphthalene is separated from the reaction mixture by the following methods. A first method comprises adding an aqueous solution of an alkaline compound, such as an aqueous solution of sodium carbonate or sodium hydrogen carbonate, to the reaction mixture to neutralize the acid catalyst contained in it, evaporating part of the organic solvent contained in the reaction mixture to form an aqueous phase and a first organic phase, separating the first organic phase, further evaporating the organic solvent from the first organic phase to concentrate it, adding a hot aromatic hydrocarbon to the concentrate to extract by-products, and precipitating 2,6-dihydroxynaphthalene as crude crystals.

Another method (second method) is the same as the first method up to the step of evaporating the organic solvent from the first organic layer to concentrate it. Thereafter, it comprises adding water to the concentrate to form a slurry containing 2,6-dihydroxynaphthalene as solids, adding an aromatic hydrocarbon to the slurry, heating the slurry to dissolve the solids, and cooling the separated and recovered aqueous phase to precipitate crude crystals of 2,6-dihydroxynaphthalene.

By concentrating the acid cleavage reaction mixture and mixing the concentrate with an aromatic hydrocarbon in the presence or absence of water, the by-products of the reaction are extracted with the aromatic hydrocarbon and removed. As a result, 2,6-dihydroxynaphthalene can be obtained as crude crystals from which most of 6-isopropyl-2-naphthol as a main by-product has been removed. As the aromatic hydrocarbon for this purpose, benzene, toluene, xylene, trimethylbenzenes, cumene, cymene, diisopropylbenzene, etc. are preferably used.

The crude crystals of 2,6-dihydroxynaphthalene may be purified, for example, by dissolving the 2,6-diisopropylnaphthalene crude crystals under heat in a solvent suitable for its purification by recrystallization to form a solution, and cooling the solution to recrystallize the crude crystals to remove tiny amounts of colored substances. As a result, nearly pure 2,6-dihydroxynaphthalene can be obtained. Examples of the recrystalization solvent are water, lower alcohols such as methanol, ethanol and propanol, aliphatic ketones such as acetone, methyl ethyl ketone and MIBK, linear or cyclic ethers such as diethyl ether, dioxane and tetrahydrofuran, acetonitrile and nitromethane. They may be used singly or in combination. Of these, water or a mixture of water and acetone having an acetone content of 0 to 90% by weight, particularly a mixture of 5 to 50% of aetone and water, is preferred.

The recrystallization solvent is used in a proportion of 0.2 to 50 parts by weight per part by weight of the 2,6-dihydroxynaphthalene crude crystals.

The resulting crystals are separated from the liquid and dried to give a pure product.

According to this invention, the 2,6-dihydroxynaphthalene formed by the acid cleavage reaction may be converted into a diacetyl compound from the reaction mixture obtained after the acid cleavage reaction and can be recovered as the diacetoxy compound. Desirably, the conversion to the diacetoxy compound is effected by a method corresponding to the first method of separating 2,6-dihydroxynaphthalene as described above in which, however, acetic anhydride is added together when adding the aromatic hydrocarbon; a method corresponding to the first and second methods in which, however, after the crude DHN is taken out, the crude DHN is added to an aromatic hydrocarbon and acetic anhydride is added in the presence of a ketone such as acetone or MIBK, acetic acid, etc.; a method in which acetic anhydride is added to the acid cleavage reaction product itself; or a method in which water is removed from the acid cleavage reaction product (which may, or may not, be neutralized), and then acetic anhydride is added.

Acetic anhydride is used in a proportion of at least 1 mole, preferably 1 to 10 moles, per mole of the hydroxyl groups of 2,6-dihydroxynaphthalene to be acetylated. The acetylation reaction may be carried out in the absence of catalyst, but usually it is carried out in the presence of an acid catalyst or a basic catalyst. Sulfuric acid and boron fluoride, for example, are preferably used as the acid catalyst. Examples of the basic catalyst are pyridine and sodium acetate. Acetyl chloride may be used in the above methods as an acetylation agent besides acetic anhydride. The acetylation reaction is carried out usually at a temperature of 0° to 200° C. After the reaction, the reaction mixture is filtered or cooled to crystallize 2,6-diacetoxynaphthalene. It is recovered as crystals by filtration.

The following examples illustrate the present invention in detail. The following abbreviations are used in these examples.

2,6-DIPN: 2,6-diisopropylnaphthalene
DHP: dihydroperoxide of 2,6-diisopropylnaphthalene
HHP: monohydroxymonohydroperoxide of 2,6-diisopropylnaphthalene
DCA: dihydroxide of 2,6-diisopropylnaphthalene
MCA: monohydroxide of 2,6-diisopropylnaphthalene
MHP: monohydroperoxide of 2,6-diisopropylnaphthalene
2,6-DHN: 2,6-dihydroxynaphthalene
2,6-DAN: 2,6-dihydroxynaphthalene diacetate

EXAMPLE 1

A 500 ml autoclave (made from SUS318L) equipped with a rotating stirrer (curved inclined paddle-type stirring vanes, vane size 55 mm in diameter), a gas blowing tube, a thermometer sheath and a reflux condenser was charged with 50 g of 2,6-diisopropylnaphthalene, 100 g of a 4.5% by weight aqueous solution of sodium hydroxide and 0.1 g of alpha,alpha'-azobis(cyclohexane-1-carbonitrile). While passing air at a rate of 20 liters/hr, the reaction was carried out for 9 hours under reaction conditions involving a temperature of 100° C., a pressure of 5 kg/cm$^2$-G and a stirrer rotating speed of 1300 rpm (peripheral speed 374 cm/sec.). After the reaction, the autoclave was opened, and the reaction mixture was taken out. Methyl isobutyl ketone (MIBK) was added to the reaction mixture to dissolve the solids, and the solution was separated into an organic phase and an aqueous phase by using a separating funnel. The aqueous phase was adjusted to pH 3 with dilute hydrochloric acid, and then extracted with diethyl ether. The organic phase and the diethyl ether extract were analyzed for composition. The results of the reaction were as follows:

Conversion of 2,6-diisopropylnaphthalene: 99.5 mole %
Yield of DHP: 15.4 mole %
Yield of HHP: 34.0 mole %
Yield of DCA: 17.1 mole %
Yield of MHP: 7.3 mole %
Yield of MCA: 4.7 mole %

EXAMPLES 2-4

Example 1 was repeated except that the concentration of NaOH in the aqueous sodium hydroxide solution was changed as shown in Table 1. The results are shown in Table 1

TABLE 1

| Example | NaOH concentration (wt. %) | DIPN conversion (mole %) | MHP | MCA | DHP | HHP | DCA | NaOH/DIPN (equivalent/mole) |
|---|---|---|---|---|---|---|---|---|
| 2 | 1 | 98.1 | 18.5 | 4.2 | 33.9 | 20.2 | 3.8 | 0.106 |
| 3 | 2 | 97.2 | 22.3 | 5.5 | 30.1 | 21.7 | 4.4 | 0.212 |
| 4 | 6 | 99.3 | 7.2 | 6.5 | 8.3 | 31.3 | 21.1 | 0.636 |

EXAMPLES 5-6

Example 1 was repeated except that an aqueous solution of each of the bases indicated in Table 2 was used instead of the 4.5% aqueous solution of sodium hydroxide. The results are shown in Table 2.

TABLE 2

| Example | Alkali | DIPN conversion (mole %) | MHP | MCA | DHP | HHP | DCA | Alkali/DINN (equivalent/mole) |
|---|---|---|---|---|---|---|---|---|
| 5 | 4.5 wt % —KOH | 99.7 | 4.9 | 3.6 | 14.9 | 26.9 | 16.0 | 0.341 |
| 6 | 5 wt % —K$_2$CO$_3$ | 96.7 | 23.6 | 5.1 | 31.4 | 17.4 | 2.9 | 0.307 |

EXAMPLE 7

(1) A 5-liter autoclave equipped with a rotating stirrer, a gas blowing tube, an alkali supply tube, a thermometer sheath and a reflux condenser was charged with 1100 g of 2,6-DIPN, 550 g of a 4.5% by weight aqueous solution of NaOH, 650 g of H$_2$O and 5.5 g of 2,6-diisopropylnaphthalene hydroperoxide (which had been formed in advance by oxidizng 2,6-DIPN and reserved as an initiator). While passing air at a rate of 195N1/hr, the reaction was carried out at a reaction temperature of 100° C., under a reaction pressure of 6 kg/cm$^2$-G, at a stirring speed of 1000 rpm. With the start of the reaction, a 10% by weight aqueous solution of NaOH was fed, and the reaction was stopped 26 hours later. The amount of the 10% by weight aqueous NaOH solution fed during this time was 1422 cc (NaOH/2,6-DIPN=0.87 equivalent/mole). After the reaction, the autoclave was opened, and the reaction mixture was taken out. To the oxidation reaction mixture, 2200 g of MIBK was added, and the mixture was separated into an oil phase (MIBK phase) and an aqueous phase. As a result of analysis by liquid chromatography, the composition of the oxidation reaction product contained in the oil phase was as follows:

| DHP | 4.3% | by weight |
|---|---|---|
| HHP | 14.7% | " |
| DCA | 9.2% | " |
| MHP | 2.3% | " |
| MCA | 1.8% | " |
| Others (molecular weight is taken as 212) | 6.0% | " |

The following results were obtained.
Conversion of 2,6-DIPN: more than 99%
Yield of DHP: 10 mole %
Yield of HHP: 36 mole %
Yield of DCA: 24 mole %
Yield of MHP: 6 mole %
Yield of MCA: 5 mole %

(2) A 2-liter glass reactor equipped with a rotating stirrer, a reflux condenser, an acid cleavage material feed tube and an acid catalyst solution feed tube was charged with 84.9 g of an acetone solution containing 1.7% by weight of $H_2SO_4$, and placed over a hot water bath at 65° C. When acetone began refluxing by heating, a mixture of 708 g of the MIBK solution of the oxidation product obtained in (1) above, 67 g of a 60% aqueous solution of hydrogen peroxide and 219 g of acetone began to be fed into the reactor through the acid cleavage material feed tube. Simultaneously with the starting of feeding the acid cleavage material, 129 g of the acetone solution containing 1.7% $H_2SO_4$ also began to be fed from the acid catalyst solution feed tube, and the feeding was finished in 1 hour. The amounts of the cleavage material and the acetone solution of $H_2SO_4$ were measured by small-sized metering pumps. Thereafter, the reaction was carried out for 3 hours.

The above acid cleavage reaction was carried out twice, and the resulting reaction mixtures were combined. Liquid chromatographic analysis showed that the acid cleavage product had the following composition.

| Acetone | 45.2% | by weight |
|---|---|---|
| MIBK | 35.2% | " |
| 2,6-Dihydroxynaphthalene | 10.3% | " |
| 6-isopropyl-2-naphthol | 1.8% | " |
| Others (the molecular is assumed to be the same as 6-isopropyl-2-naphthol) | 4.0% | " |
| Water | 3.5% | " |

(3) Then, 2000 g of the acid cleavage reaction mixture was taken, and to neutralize $H_2SO_4$ contained in it, a 2% aqueous solution of sodium carbonate was gradually added until the pH of the solution reached about 4. Then, to remove acetone and MIBK contained in the acid cleavage reaction mixture, the following concentrating operation was carried out.

Acetone was first evaporated under atmospheric pressure by means of a rotary evaporator to obtain an aqueous phase and an oil phase. The oil layer was separated from the aqueous layer and again subjected to a rotary evaporator under a reduced pressure of 20 to 30 mmHg to evaporate MIBK and obtain a concentrate. This concentrate contained 45.7% by weight of 2,6-dihydroxynaphthalene and 8.0% by weight of 6-isopropyl-2-naphthol.

A 2-liter separable flask equipped with a rotating stirrer, a thermometer and a reflux condenser was charged with 400 g of the above concentrate and 1200 g of cumene, and placed over a hot water bath at 70° C. The contents of the flask were stirred at the same temperature for 15 minutes. Then, the temperature of the hot water bath was gradually lowered to precipitate crystals further. Finally, it was cooled to room temperature to precipitate the crystals fully. Thereafter, the crystals were separated by filtration, and dried to give 236 g of crude crystals of 2,6-dihydroxynaphthalene (the ratio of 2,6-dihydroxynaphthalene crystals recovered 96.8%). The resulting crude crystals contained 75.0% by weight of 2,6-dihydroxynaphthalene and 0.9% by weight of 6-isopropyl-2-naphthol.

Twenty-five grams of the dried crude crystals were added to 100 g of an acetone/water (20/80) mixed solvent and heated to 60° C. to dissolve them. The crystals were separated by filtration, and dried under reduced pressure. The purity of the 2,6-dihydroxynaphthalene crystals, determined by gas chromatographic analysis, was 99.0%, and the 2,6-dihydroxynaphthalene crystals had a melting point of 220.5° to 222.5° C.

EXAMPLE 8

(1) A 500 ml autoclave (made from SUS 316L) equipped with a rotating stirrer, a gas blowing tube, a thermometer and a reflux condenser was charged with 50 g of 2,6-diisopropylnaphthalene, 100 g of a 4.5% aqueous solution of sodium hydroxide and 0.1 g of alpha,alpha'-bis(cyclohexane-1-carbonitrile). While air was blown at a rate of 20 liters/hour with intense stirring of the contents, the reaction was carried out at a reaction temperature of 100° C. under a pressure of 5 $kg/cm^2$-G for 9 hours. The conversion of 2,6-diisopropylnaphthalene was 99.3%.

Methyl isobutyl ketone (100 g) was added to the resulting oxidation reaction product, and the oil phase (methyl isobutyl ketone phase) was separated from the aqueous phase.

The above oxidation reaction was then carried out three times in the same way, and the resulting oily layers of the oxidation reaction products were combined. The conversions of 2,6-diisopropylnaphthalene in these reactions were 99.5%, 99.4%, and 99.2%, respectively. The oxidation product contained in the combined oily phase was determined to be as follows by liquid chromatographic analysis.

| DHP | 5.6% by weight |
|---|---|
| HHP | 12.3% by weight |
| DCA | 6.4% by weight |
| MHP | 2.8% by weight |
| MCA | 1.7% by weight |
| Others (the molecular weight is assumed to be 212) | 7.6% by weight |

The water content of the oily phase was 3.0% as a result of analysis by the Karl-Fischer's method. The amount of the alkali was 15 ppm.

(2) Then, a 300 ml glass reactor equipped with a rotating stirrer, a reflux condenser, an acid cleavage material feed tube and an acid catalyst solution feed tube was charged with 6.6 g of an acetone solution containing 1.7% by weight of sulfuric acid. The reactor was placed over a hot water bath kept always at 65° C. When acetone began refluxing by heating, a mixture of 55 g of the MIBK solution of the oxidation product (oil phase), 4.0 g of a 60% aqueous solution of hydrogen peroxide and 17 g of acetone began to be fed from the acid cleavage material feed tube. Simultaneously with the starting of feeding the acid cleavage material, 10 g of an acetone solution containing 1.7% of sulfuric acid began to be fed from the acid catalyst solution feed tube, and the feeding was finished in 1 hour. The amounts of the cleavage material and the acetone solution of sulfuric acid fed were determined by small-size metering pumps. Thereafter, the reaction was carried out for 3 hours.

After the reaction, the acid cleavage reaction product was analyzed by liquid chromatography and gas chromatography, and found to contain 9.6% by weight of 2,6-dihydroxynaphthalene. Accordingly, the result of the re-oxidation and acid cleavage using hydrogen peroxide was that the yield of 2,6-dihydroxynaphthalene is 99.5 mole % based on DHP, HHP and DCA contained in the acid cleavage material. The overall yield of 2,6-dihydroxynaphthalene based on the 2,6-diisopropylnaphthalene charged was 62 mole %.

EXAMPLE 9

In Example 8, the reoxidation and acid cleavage reaction of the acid cleavage material using hydrogen peroxide were carried out in the same way as in Example 8, (2) except that a portion of the MIBK solution (oily phase) of the oxidation reaction product obtained in Example 8, and 2.7 g [0.8 mole per mole of (HHP+DCAx2+MCA)] of a 60% aqueous solution of hydrogen peroxide were used.

After the reaction, the acid cleavage reaction mixture contained 7.8% by weight of 2,6-dihydroxynaphthalene. Analysis of the reaction mixture by liquid chromatography and gas chromatography showed that the reaction mixture contained by-products resulting from condensation of the carbinols in addition to the unreacted HHP, DCA and MCA. The result of this reaction was that the yield of 2,6-dihydroxynaphthalene was 80 mole %.

The same reaction was carried out using varying amounts of hydrogen peroxide. The results are shown in Table 3. Table 3 also gives the results obtained in Example 8 above.

TABLE 3

| Amount of hydrogen peroxide (moles)[1] | Yield of DHN (mole %)[2] | Formation of condensates of the carbinols |
|---|---|---|
| 0.8 | 80 | Yes |
| 0.9 | 90 | Yes |
| 1.0 | 98 | Very little |
| 1.2[3] | 99.5 | No |
| 1.5 | 99.5 | No |

Note
[1] per mole of (HHP + DCA + 2 × MCA)
[2] DHN represents 2,6-dihydroxynaphthalene.
[3] the results of Example 8

EXAMPLE 10

A portion of the MIBK solution (oily phase) of the oxidation product obtained in Example 8 was taken, washed twice with water, and used in acid cleavage reaction.

The reaction was carried out in the same way as in Example 8, (2) except that phosphotungstic acid was used instead of sulfuric acid as the acid catalyst, and the concentration of phosphotungstic acid in its acetone solution was adjusted to 0.6% by weight.

The acid cleavage reaction mixture contained 9.0% by weight of 2,6-dihydroxynaphthalene. The result in the reoxidation and acid cleavage using hydrogen peroxide was that the yield of 2,6-dihydroxynaphthalene is 94 mole % based on DHP, HHP and DCA contained in the cleavage material.

COMPARATIVE EXAMPLE 1

(1) The same autoclave as used in Example 8, (1) was charged with 75 g of 2,6-diisopropylnaphthalene, 75 g of a 1% aqueous solution of sodium hydroxide and 0.1 g of alpha,alpha'-bis(cyclohexane-1-carbonitrile). While air was blown at a rate of 20 liters/hour with intense stirring of the contents, the reaction was carried out for 5 hours at a reaction temperature of 100° C. under a pressure of 5 kg/cm$^2$-G. The conversion of 2,6-diisopropylnaphthalene was 72%.

The resulting reaction product was reacted in the same way as in Example 8, (1) to give an oily phase containing the oxidation product.

The oxidation product in the oily phase had the following composition.

| DHP | 2.1% by weight |
|---|---|
| HHP | 3.5% by weight |
| DCA | 0.9% by weight |
| MHP | 14.0% by weight |
| MCA | 5.1% by weight |
| Others (the molecular weight is assumed to be 212) | 1.0% by weight |

(2) Acid cleavage reaction was carried out subsequently under the same reaction conditions as in Example 8, (2) using the same apparatus as used therein. Hydrogen peroxide was used in an amount equal to the theoretically required amount (HHP+DCAx2+MCA). After the acid cleavage reaction, the yield of 2,6-dihydroxynaphthalene (based on DHP, HHP and DCA contained in the acid cleavage material) was 97.5%. The overall yield of 2,6-dihydroxynaphthalene based on the 2,6-diisopropylnaphthalene charged in the oxidation reaction was 16 mole %.

EXAMPLE 11

(1) A 500 ml autoclave (SUS 316L) equipped with a rotating stirrer, a gas blowing tube, a thermometer and a reflux condenser was charged with 75 g of 2,6-diisopropylnaphthalene, 75 g of a 4.5% aqueous solution of sodium hydroxide and 0.1 g of alpha,alpha'-bis(cyclohexane-1-carbonitrile). While air was blown at a rate of 20 liters/hour with intense stirring of the contents, the reaction was carried out for 9 hours at a reaction temperature of 100° C. under a pressure of 5 kg/cm$^2$-G. The conversion of 2,6-diisopropylnaphthalene as 99.5%.

Methyl isobutyl ketone (150 g) was added to the oxidation reaction product, and the oily layer (methyl isobutyl ketone phase) was separated from the aqueous phase. The oxidation product contained in the oily phase had the following composition as a result of analysis by liquid chromatography.

| DHP | 6.5% by weight |
|---|---|
| HHP | 13.4% by weight |

| | |
|---|---|
| DCA | 6.3% by weight |
| MHP | 2.7% by weight |
| MCA | 1.6% by weight |
| Others (the molecular weight is assumed to be 212) | 7.6% by weight |

(2) Then, a 300 ml glass reactor equipped with a rotating stirrer, a reflux condenser, an acid cleavage material feed tube and an acid catalyst solution feed tube was charged with 28.3 g of an acetone solution containing 1.7% by weight of sulfuric acid. The reactor was placed over a hot water bath kept always at 65° C. When acetone began refluxing by heating, a mixture of 236 g of the MIBK solution (oil phase) of the oxidation product, 17.2 g of a 60% aqueous solution of hydrogen peroxide and 73 g of acetone began to be fed from the acid cleavage material feed tube. Simultaneously with the starting of feeding the acid cleavage material, 43 g of an acetone solution containing 1.7% of sulfuric acid began to be fed from the acid catalyst solution feed tube, and the feeding was finished in 1 hour. The amounts of the cleavage material and the acetone solution of sulfuric acid fed were determined by small-size metering pumps. Thereafter, the reaction was carried out for 3 hours.

The above acid cleavage reaction was carried out twice, and the resulting reaction mixtures were combined. As a result of analysis by liquid chromatography, the acid cleavage reaction product had the following composition.

| | |
|---|---|
| 2,6-dihydroxynaphthalene | 9.6% by weight |
| 6-isopropyl-2-naphthol | 2.0% by weight |
| 2,6-diisopropylnaphthalene | 0.1% by weight |
| Others (the molecular weight is assumed to be the same as 6-isopropyl-2-naphthol) | 4.0% by weight |

(3) Then, 150 g of the acid cleavage reaction mixture was taken, and in order to neutralize sulfuric acid contained in it, a 2% aqueous solution of sodium carbonate was gradually added until the pH of the solution reached about 4. Then, to remove acetone and MIBK contained in the acid cleavage reaction mixture, the following concentrating operation was carried out. First, acetone was evaporated under atmospheric pressure by means of a rotary evaporator to obtain an aqueous phase and an oil phase. The oil phase was separated from the aqueous phase, and again subjected to a rotary evaporator under a reduced pressure of 20 to 30 mmHg to evaporate MIBK and to obtain a concentrate. Evaporation of MIBK was stopped just before the crystals began to precipitate.

The concentrate contained 21.6% by weight of 2,6-dihydroxynaphthalene and 4.4% by weight of 6-isopropyl-2-naphthol.

A 500 ml separable flask equipped with a stirrer, a thermometer, a reflux condenser and a concentrate dropping opening was charged with 290 g of cumene, and placed on a hot water bath at 70° C. The above concentrate (69 g) was gradually added dropwise to the flask to precipitate crystals. After the addition, the temperature of the hot water bath was gradually lowered to precipitate the crystals further. Finally, it was cooled to room temperature to precipitate the crystals fully.

The crystals were then separated by filtration and dried to give 23 g of crude crystals of 2,6-dihydroxynaphthalene (the ratio of 2,6-dihydroxynaphthalene crystals recovered 80%). The crude crystals contained 50.7% by weight of 2,6-hydroxynaphthalene and 0.7% by weight of 6-isopropyl-2-naphthol.

EXAMPLE 12

One hundred grams of the acid cleavage reaction mixture obtained in Example 11, (1) was taken, and as in Example 11, (1), treated with a 2% aqueous solution of sodium carbonate to neutralize sulfuric acid. Then, acetone was evaporated to form an aqueous phase and an oily phase. The oily phase was separated from the aqueous phase.

The separated oily phase was charged into a 300 ml separable flask equipped with a stirrer, a thermometer, a distillate withdrawing device and a dropping funnel, and the flask was placed over an oil bath kept at 100° to 110° C. MIBK was removed as an azeotrope with water. Water was occasionally supplied from the dropping funnel to make up for the water drawn from the reaction mixture with the distillation of the azeotropic mixture. After MIBK was evaporated, the reaction mixture become slurry-like.

Water was added to this slurry containing 2,6-dihydroxynaphthalene to adjust the total amount to 130 g. The slurry was then transferred to a 300 ml glass autoclave. Fifty grams of cumene was introduced into the autoclave. After the pressure of the inside of the autoclave was elevated to 5 kg/cm$^2$-G with nitrogen, the mixture was heated to 160° C. and stirred. After the solids were completely dissolved, heating and stirring were stopped, and the mixture was allowed to stand. The oily phase was drawn from the mixture. Stirring of the contents was resumed and the contents were allowed to cool. When the contents nearly reached room temperature, they were taken out and filtered to give 11.5 g of wet crude crystals of 2,6-dihydroxynaphthalene. The crude crystals contained 1.2%, based on 2,6-dihydroxynaphthalene, of 6-isopropyl-2-naphthol.

The crude crystals (11 g) were dissolved in 135 g of a 20% aqueous solution of acetone, and subjected to active carbon treatment and purification by recrystallization as in Example 11 to give 8.1 g of purified 2,6-dihydroxynaphthalene as crystals having a purity of 99.8% and a melting point of 220.9° to 222.0° C.

EXAMPLE 13

Sixty parts by weight of acetone was added to 100 parts by weight of the oily phase containing the oxidation product obtained in Example 8, (1) to prepare an MIBK/acetone mixed oily phase which was subjected to acid cleavage by the following method to obtain 2,6-dihydroxynaphthalene.

A 300 ml glass reactor equipped with a rotating stirrer, a reflux condenser, an acid cleavage material feed tube and an acid catalyst solution feed tube was charged with 6.6 g of an acetone solution containing 1.7% by weight of sulfuric acid. The reactor was placed over a hot water bath always maintained at 65° C. When acetone began to be refluxed by heating, feeding of a mixture of 72 g of the MIBK/acetone mixed oily phase of the oxidation product and 4.0 g of a 60% aqueous solution of hydrogen peroxide from the acid cleavage material feed tube was started. Simultaneously with the feeding of the acid cleavage material, 10 g of an acetone solution containing 1.7% sulfuric acid began to be fed from the acid catalyst solution feed tube, and the feeding was finished in 1 hour. The amounts of the acid cleavage material and the acetone solution of sulfuric acid were determined by small-sized metering pumps. Thereafter, the reaction was further carried out for 3 hours.

As a result of analysis by liquid chromatography and gas chromatography after the reaction, the acid cleavage reaction product contained 9.6% by weight of 2,6-dihydroxynaphthalene. Accordingly, the result of the reaction in this case was that the yield of 2,6-dihydroxynaphthalene is 99.5 mole % based on DHP, HHP and DCA contained in the acid cleavage material. The overall yield of 2,6-dihydroxynaphthalene based on the charged 2,6-diisopropylnaphthalene was 62 mole %.

EXAMPLE 14

The oily phase composed of an MIBK layer containing the oxidation reaction product obtained by the method of Example 8, (1) was distilled at 100 mmHg and 80° C. finally, and water remaining in the oily layer was removed as an azeotrope with MIBK to adjust the concentration of water in the oily layer to less than 1000 ppm as measured by the Karl-Fischer's method. Thereafter, the oily phase was subjected to acid cleavage in the same way as in Example 13. The results are shown in Table 4.

TABLE 4

| | | Oil phase | | Yield of |
| --- | --- | --- | --- | --- |
| Example | Solvent | Oil-water separating operation | Amount of the alkali (ppm) | Water content (ppm) | 2,6-dihydroxynaphthalene (%) |
| 13 | MIBK | Easy | 15 | 30000 | 99.5 |
| 14 | " | " | 15 | <1000 | 99.6 |

EXAMPLE 15

The acid cleavage reaction product obtained in Example 7 [composition: acetone 45.2% by weight, MIBK 35.2% by weight, 2,5-dihydroxynaphthalene 10.3% by weight, 6-isopropyl-2-naphthol 1.8% by weight, others (the molecular weight is assumed to be the same as 6-isopropyl-2-naphthol) 4.0% by weight, and water 3.5% by weight] was concentrated under reduced pressure to remove acetone and MIBK and obtain a concentrate. Cumene (40 g) was added to 40 g of the concentrate, and 40 g of acetic anhydride was added. With stirring, sulfuric acid was added dropwise to the mixture until its concentration in the mixture reached 500 ppm. The mixture was then heated to 130° C., and after it began to be refluxed, reacted for hour. The reaction mixture was allowed to cool to 20° C., and separated into the crystals and the filtrate. From the diacetoxynaphthalene (2,6-DAN) contents of the two, the conversion and the yield of the crystals were determined. It was found that the conversion was 99 mole % (based on 2,6-DHN), the yield of the crystals obtained was 95 mole %, and the purity of the crystals was 99.5%.

EXAMPLES 16–18

The concentrate obtained in Example 15 was treated in the same way as in Example 15 except that acetone, methyl isobutyl ketone (MIBK), or acetic acid was used instead of cumene. The results are shown in Table 5.

TABLE 5

| Example | Solvent (40 g) | Reaction temperature (°C.) | Reaction Yield (%) | Yield of the crystals obtained (%) | Purity (%) |
| --- | --- | --- | --- | --- | --- |
| 16 | Acetone | 60 | 99.2 | 90 | 99.6 |
| 17 | " | 130 | 99.7 | 95 | 99.6 |
| 18 | Acetic Acid | 130 | 99.5 | 96 | 99.4 |

EXAMPLE 19

One hundred grams of the acid cleavage product before neutralization obtained in Example 7 was fed into a 300 ml glass reactor equipped with a rotating stirrer, a reflux condenser and a dropping funnel, and the reactor was placed over a hot water bath at 65° C. When acetone began to be refluxed by heating, dropwise addition of acetic anhydride was started. After adding 45 g of acetic anhydride dropwise over 1 hour, the mixture was reacted at 60° C. for 130 minutes. As a result of analysis by liquid chromatography, the concentration of 2,6-diacetoxynaphthalene (2,6-DAN) was 10.7% by weight. The yield of 2,6-DAN based on DHN was 99.7 mole %. Acetone was evaporated from the reaction mixture, and the residue was cooled to 20° C. and separated into the crystals and the filtrate. It was found that the yield of the crystals obtained was 87 mole %, and their purity was 99.3%.

EXAMPLE 20

The neutralized acid cleavage product (200 g) obtained in Example 7 was used, and acetone was evaporated from it, and then it was separated into an oily phase (MIBK solution) having the following composition and an aqueous phase.

| Composition of the MIBK solution | |
| --- | --- |
| MIBK | 60.8% by weight |
| DHN | 25.1% by weight |
| MHN | 4.4% by weight |
| Others | 9.7% by weight |

Some water contained in the oily phase was removed by azeotropic distillation, and the resulting MIBK solution (50 g) and 22.5 g of acetic anhydride were fed into a 300 ml glass reactor equipped with a rotating stirrer, a reflux condenser and a dropping funnel. With stirring, sulfuric acid was added dropwise to the mixture until its concentration in the mixture reached 500 ppm. The mixture was then heated to 130° C., and after it began to be refluxed, reacted for one hour. As a result of analysis by liquid chromatography, the concentration of 2,6-DAN was 26.3% by weight, and the yield of 2,6-DNA was 99.7 mole %. The reaction mixture was allowed to cool to 20° C. and separated into the crystals and the filtrate, and the yield and purity of the crystals were determined. It was found that the yield of the crystals obtained was 91 mole %, and their purity was 99.2%.

EXAMPLE 21

The MIBK solution obtained in Example 7, (1) was washed twice with water in an amount of 25% by weight. The resulting MIBK solution was dehydrated and concentrated continuously by an evaporator at 80° C. and 50 mmHg. Acetone was added to the concentrate in an amount corresponding to the amount of acetone which distilled out. Thus, an acid cleavage material was prepared.

A 2-liter glass reactor equipped with a rotating stirrer, a reflux condenser, an acid cleavage material feed tube and an acid catalyst solution feed tube was charged with 143.1 g of an acetone solution containing 0.43% by weight of $H_2SO_4$, and placed over a hot water bath at 65° C. When acetone began to be refluxed by heating, feeding of a mixture of 800 g of the acid cleavage material, 90.6 g of a 60% aqueous solution of hydrogen peroxide and 250 g of acetone from the acid cleavage material feed tube was started. Simultaneously with the starting of feeding the acid cleavage material, feeding of 214.7 g of an acetone solution containing 0.43% by weight of $H_2SO_4$ from the acid catalyst feed tube was started, and finished in 1 hour. The amounts of the cleavage material and the acetone solution of sulfuric acid were determined by small-sized metering pumps. Thereafter, the reaction was further carried out for 2 hours.

The above acid cleavage reaction was carried out three times, and the resulting reaction mixtures were combined. As a result of analysis by liquid chromatography, the acid cleavage product contained 10.0% by weight of 2,6-dihydroxynaphthalene, 1.7% by weight of 6-isopropyl-2-naphthol, and 1.7% by weight of others (the molecular weight is assumed to be the same as 6-isopropyl-2-naphthol).

Four thousand grams of the acid cleavage reaction mixture was taken, and to neutralize sulfuric acid contained in it, a 2% aqueous solution of $NaHCO_3$ was gradually added until the pH of the solution reached about 4. Thereafter, to remove acetone and MIBK contained in the acid cleavage reaction mixture, the following concentrating operation was performed.

Specifically, acetone was first evaporated under atmospheric pressure by means of a rotary evaporator to form an aqueous phase and an oily phase. The oily phase was separated from the aqueous phase. The separated oily phase was washed with 10% by weight, based on the oily phase, of water, and again subjected to a rotary evaporated under a reduced pressure of 20 to 30 mmHg to evaporate MIBK and give a concentrate.

Then, a 2-liter separable flask equipped with a rotating stirrer, a thermometer and a reflux condenser was charged with 400 g of the above concentrate and 120 g of cumene, and placed over a hot water bath at 70° C. The mixture was stirred at the same temperature for 15 minutes, and then the temperature of the water bath was gradually lowered. At 50° C., the crystals were separated by filtration. The resulting crude crystals contained 45.4% by weight of 2,6-dihydroxynaphthalane (the rate of recovering 2,6-dihydroxynaphthalene 100%).

Then, 500 g of the resulting crude crystals and 500 g of cumene were introduced into a 2-liter separable flask equipped with a rotary stirrer, a thermometer and a reflux condenser. Then, 388.5 g of acetic anhydride was added. The reactor was placed on an oil bath at 135° C., and with stirring, sulfuric acid was added dropwise so that its concentration in the reaction mixture reached 500 ppm. The mixture was then heated to 130° C., and after it began to be refluxed, reacted for 1 hour. The reaction mixture was analyzed by liquid chromatography, and found to contain 24.9% by weight of 2,6-DAN. The yield of 2,6-DAN based on DHN was 99.9 mole %.

The reaction mixture was gradually cooled to 20° C. and separated into the crystals and the filtrate. The resulting crystals were rinsed with acetone.

As a result, the yield of the 2,6-DAN crystals obtained was 90 mole %, and their purity was 99.2%.

What is claimed is:

1. A process for producing 2,6-dihydroxynaphthalene, which comprises:
   (1) oxidizing 2,6-diisopropylnaphthalene with molecular oxygen in a reaction system having an aqueous phase containing a base to form oxidation reaction products comprising dihydroperoxide, monohydroxymonohydroperoxide and dihydroxide of 2,6-diisopropylnaphthalene, said oxidation being conducted at a pH of between 11 and 14, said base being added as an aqueous solution having a concentration of 1 to 25% by weight in an amount to provide 0.2 to 1.0 gram-equivalent of said base per mole of said 2,6-diisopropylnaphthalene; and
   (2) subjecting the resultant mixture containing said reaction products to acid cleavage in the presence of hydrogen peroxide to obtain 2,6-dihydroxynaphthalene.

2. The process according to claim 1, wherein said base is added in divided portions to said aqueous phase, one portion of the base being added to the aqueous phase before the start of the oxidation and the remaining portions being added to the aqueous phase during the oxidation.

3. The process according to claim 1, wherein said base is sodium hydroxide.

4. The process according to claim 2, wherein said base is sodium hydroxide.

5. The process according to claim 1, wherein said oxidation is continued until at least 99% by weight of said 2,6-diisopropylnaphthalene is oxidized.

6. The process according to claim 2, wherein said oxidation is continued until at least 99% by weight of said 2,6-diisopropyl naphthalene is oxidized.

7. The process according to claim 3, wherein said oxidation is continued until at least 99% by weight of said 2,6-diisopropylnaphthalene is oxidized.

8. The process according to claim 4, wherein said oxidation is continued until at least 99% by weight of said 2,6-diisopropylnaphthalene is oxidized.

9. A process for producing 2,6-dihydroxynaphthalene from 2,6-diisopropylnaphthalene, which comprises:
   (1) oxidizing 2,6-diisopropylnaphthalene with molecular oxygen in a reaction system having an aqueous phase containing a base to form oxidation reaction products comprising dihydroperoxide, monohydroxymonohydroperoxide and dihydroxide of 2,6-diisopropylnaphthalene, said oxidation being conducted at a pH of between 11 and 14, said base being added as an aqueous solution having a concentration of 1 to 25% by weight in an amount to provide 0.2 to 1.0 gram-equivalent of said base per mole of said 2,6-diisopropylnaphthalene;
   (2) adding a water-insoluble or sparingly water-soluble ketone to said reaction system to form an organic phase and an aqueous phase;
   (3) separating said organic phase from said aqueous phase; and
   (4) subjecting said separated organic phase to acid cleavage in the presence of hydrogen peroxide.

10. The process according to claim 9, wherein said reaction system further comprises an organic solvent and, prior to said addition of said water-insoluble or sparingly water-soluble ketone to said reaction system, said organic solvent is separated from said reaction system.

11. The process according to claim 9, wherein, prior to acid cleavage, said separated organic phase is subjected to azeotropic distillation to remove at least part of any water contained therein.

12. The process according to claim 11, wherein, prior to said acid cleavage and subsequent to said azeotropic distillation, acetone is added to said organic phase.

* * * * *